United States Patent
Brassil

(10) Patent No.: US 9,320,269 B2
(45) Date of Patent: Apr. 26, 2016

(54) ORGAN PRESERVATION SYSTEM

(76) Inventor: John Brassil, Northbrook, IL (US)

( * ) Notice: Subject to any disclaimer, the term of this patent is extended or adjusted under 35 U.S.C. 154(b) by 346 days.

(21) Appl. No.: 12/890,426

(22) Filed: Sep. 24, 2010

(65) Prior Publication Data

US 2011/0076666 A1    Mar. 31, 2011

Related U.S. Application Data

(60) Provisional application No. 61/245,898, filed on Sep. 25, 2009.

(51) Int. Cl.
*C12M 1/00* (2006.01)
*A01N 1/00* (2006.01)
*A01N 1/02* (2006.01)

(52) U.S. Cl.
CPC .................................. *A01N 1/0247* (2013.01)

(58) Field of Classification Search
CPC .... C12M 27/02; C12M 21/08; A01N 1/0236; A01N 1/0247
See application file for complete search history.

(56) References Cited

U.S. PATENT DOCUMENTS

| | | | |
|---|---|---|---|
| 3,654,085 A | | 4/1972 | Norr et al. |
| 3,772,153 A | * | 11/1973 | De Roissart ............... 435/284.1 |
| 4,649,114 A | * | 3/1987 | Miltenburger et al. ....... 435/401 |
| 4,879,283 A | | 11/1989 | Belzer et al. |
| 5,032,524 A | * | 7/1991 | Buntemeyer et al. ......... 435/400 |
| 5,157,930 A | | 10/1992 | McGhee et al. |
| 5,326,706 A | | 7/1994 | Yland et al. |
| 5,338,662 A | | 8/1994 | Sadri |
| 5,385,821 A | | 1/1995 | O'Dell et al. |
| 5,843,024 A | | 12/1998 | Brasile |
| 5,871,464 A | | 2/1999 | Tryggvason et al. |
| 5,941,841 A | | 8/1999 | Mutch |
| 5,965,433 A | | 10/1999 | Gardetto et al. |
| 6,027,498 A | | 2/2000 | Mutch |
| 6,100,082 A | | 8/2000 | Hassanein |
| 6,642,045 B1 | | 11/2003 | Brasile |
| 6,673,594 B1 | | 1/2004 | Owen et al. |
| 6,905,871 B1 | * | 6/2005 | Doorschodt et al. ........ 435/284.1 |
| 6,977,140 B1 | | 12/2005 | Owen et al. |
| 7,176,015 B2 | | 2/2007 | Alford et al. |
| 7,250,292 B2 | | 7/2007 | Fahy |
| 7,504,201 B2 | | 3/2009 | Taylor et al. |
| 2005/0221269 A1 | * | 10/2005 | Taylor et al. .................... 435/1.1 |
| 2009/0291486 A1 | * | 11/2009 | Wenrich ....................... 435/284.1 |

\* cited by examiner

*Primary Examiner* — Nathan Bowers

(57) ABSTRACT

An organ preservation system having an organ chamber with a perfusate reservoir surrounded by a heat exchanger. The system has a pump for circulating perfusate, which draws perfusate from the reservoir and passes the perfusate through a bubble trap, and temperature and pressure sensors prior to entering the chamber where the organ is perfused. An oxygenator with a platform and a filter is situated within the perfusate reservoir such that perfusate leaving the organ which rests on the platform passes through the filter before dripping into the perfusate reservoir below. The pump recirculates perfusate from the perfusate reservoir. The oxygenator has gas permeable tubes wound around support legs of the oxygenator. Circulation of oxygen through the tubes allows for gas exchange by diffusion across the membrane to oxygenate perfusate flowing around the tubes.

2 Claims, 7 Drawing Sheets

ORGAN PRESERVATION SYSTEM

This application claims the benefit of U.S. Provisional Patent Application No. 61/245,898, filed Sep. 25, 2009, with a title of "Organ Preservation System", and a first named inventor of John M. Brassil, which is herein incorporated by reference.

FIELD OF THE INVENTION

This invention relates in general to the field of ex vivo organ preservation, particularly for the purposes of organ transplantation and medical research.

BACKGROUND OF THE INVENTION

Improved methods of suppressing immune rejection of the transplanted organ by the transplant recipient have made organ donation an increasingly feasible medical procedure since the 1970's. Accordingly, the area of organ preservation has grown in conjunction with the increased success rates of organ transplantation.

The science of organ preservation seeks to maintain the donor organ, once it has been removed from the donor, in a viable condition by artificial means. This ex vivo preservation is done to maintain the organ until a recipient is selected and prepared to receive the organ. During preservation, analysis can be performed on the organ to assess its viability for transplantation, or to match an organ with a recipient. The ability to preserve the organ for longer times would improve the success rate of donor organs, and allow organs to reach a broader base of recipients in need. Organ preservation systems also allows for strategies which improve the function of transplants to be performed.

Ex vivo preservation can also be used to preserve an organ for medical research purposes or to pre-treat a transplantable organ to enhance its viability and functionality post-transplantation.

Various prior art patents detail aspects of organ preservation. U.S. Pat. Nos. 5,941,841, 6,027,498, and 5,326,706 describe methods of controlling biological fluid. U.S. Pat. Nos. 6,100,082, 6,673,594, 5,338,662, 3,654,085, 7,176,015, and 5,385,821 describe devices and methods associated with the preservation of organs. Support systems and methods that can be used to repair damage to organs are disclosed in U.S. Pat. Nos. 6,642,045 and 5,843,024. U.S. Pat. No. 5,965,433 discloses a device to oxygenate the perfusate. U.S. Pat. Nos. 7,504,201 and 5,871,464 discuss the preservation of organs for purposes other than organ transplantation. Solutions for preservations of organs or tissues are described in U.S. Pat. Nos. 7,250,292 and 4,879,283.

U.S. Pat. Nos. 5,941,841 and 6,027,498 describe the control of a blood pump flow output during cardiopulmonary bypass to mimic normal pulsatile flow from the heart and control of a ventilator output to mimic normal breathing of healthy lungs. A pattern of variation of time of a biological fluid to an organ of a mammalian species is established. A variable control parameter for regulation of flow of biological fluid to the organ is generated in accordance with the pattern, and the flow of biological fluid to the organ is controlled in accordance with the variable control parameter.

U.S. Pat. No. 5,326,706 discloses a organ preservation system and a method of perfusing the donor organ. Perfusion of the donor organ comprises the use of a pressure sensor to determine the vascular resistance of the organ. The perfusion pump control responds to sensor signals and adjusts the pulse rate accordingly. The pulse rate of the pump is decreased if the resistance of the perfused organ increases, and vice versa.

In U.S. Pat. No. 6,100,082, a perfusion apparatus for maintaining a harvested organ during a preservation period is disclosed. U.S. Pat. No. 6,100,082 teaches an apparatus comprising a preservation chamber, and a perfusion circuit with a line for providing an oxygenated fluid to the organ, and a second line for carrying depleted fluid from the organ. U.S. Pat. Nos. 6,673,594 and 6,977,140 describe an organ perfusion apparatus and method for perfusing an organ that monitors, sustains, and/or restores the viability of the organ, and discloses a transporting or storing apparatus. In U.S. Pat. No. 3,654,085, a pressure chamber for storing organic transplants and supplying the transplants with oxygenated blood is provided with an oxygenator and a blood pump inside the chamber. In U.S. Pat. No. 7,176,015, a chilled oxygenated nutrient solution is perfused in a transportable organ preservation system. U.S. Pat. No. 5,385,821 discloses a method and apparatus for preserving tissue ex vivo. The tissue preservation devices includes a gas permeable membrane and perfusate which oxygenates the tissue.

In U.S. Pat. No. 5,338,662, a device, and methods for perfusing organs by controlling either the perfusion pressure or the perfusate flow rate is disclosed. Devices and methods for perfusing multiple organs simultaneously on the same device are also disclosed.

In U.S. Pat. No. 6,642,045, a metabolic support system for maintaining an organ or tissue at near metabolic rate is disclosed. The support system utilizes a warm perfusion solution. U.S. Pat. No. 5,843,024 discloses a process and a solution for resuscitation to induce repair of is chemically damaged organs and tissues.

U.S. Pat. No. 5,965,433 discloses a perfusion device coupled with an oxygenator module. The perfusion apparatus uses compressed oxygen to push perfusate pumping piston to pump the perfusate through an oxygenator. The piston strokes are in an arrangement to allow for continuous supply of oxygen to the oxygenator, while slowly discharging perfusate through the oxygenator.

U.S. Pat. No. 7,504,201 discloses a method for perfusing an organ to preserve the organ in order to perform further studies on, or with the organ. An organ is perfused with a first medical fluid, and then a second medical fluid to introduce a substance into the organ to create a reaction between the organ and the substance. U.S. Pat. No. 5,871,464 discusses the delivery of a viral vector gene therapy pharmaceutical to ex vivo tissue.

In U.S. Pat. No. 7,250,292, the use of a hypertonic solution to reduce injury to tissue that is caused by cooling and warming of tissue is disclosed. The hypertonic solution is used prior to preservation cooling of tissue. U.S. Pat. No. 4,879,283 describes a solution for the preservation of organs using a perfusate or storage solution containing a specific synthetic hydroxyethyl starch in place of human serum albumin.

Each of the foregoing patents is hereby incorporated by reference except where the teaching is inconsistent with the present disclosure.

The present inventor has recognized that known prior art organ preservation systems have been disadvantageous for various reasons. Prior art organ preservation systems lack a versatility that allows the user to accommodate various types of organs, for purposes of both organ preservation for transplantation and for medical research. Prior art systems also do not provide organ preservation devices which can be used to perfuse the donor, or allow a donor to benefit from the functionality of an ex vivo organ that may not be suitable for transplantation.

The present inventor has recognized that prior art systems lack a compact design and efficiency. Prior art configurations do not incorporate an oxygenator with the heat exchanger as in the present invention. The present inventor recognizes a need for a compact system that is easy to use and maintain. The present inventor further recognizes a need for a system that utilizes autoclave sterilizable parts that can be reused, thus reducing the costs associated with organ preservation.

SUMMARY OF THE INVENTION

The invention includes an organ preservation system and a method of using that system. The method involves isolating an organ, such as kidney, liver, heart, lung or pancreas, or tissue, from its normal physiological environment. The organ is excised at the point of the arterial source of blood feeding into the organ, and at the venous outflow from the organ. The organ is flushed with perfusate, and prepared to receive perfusate in accordance with embodiments of the invention.

The system employs a perfusion solution capable of supporting metabolism of the organ or tissue, thus preserving its functionality. The system monitors parameters of the circulating perfusion solution, such as temperature, pressure, electrolyte level, glucose and lactate levels In one embodiment, the organ preservation system includes an organ chamber section, a base, a pump, a bubble trap, and a control section.

In one embodiment, the organ chamber section comprises a transparent material that can be autoclave sterilized. The organ chamber can be in the shape of a sphere, cylinder, or other sizes to accommodate various shapes and sizes of the organ to be preserved. A bottom portion of the organ chamber contains a perfusate reservoir where the perfusate is oxygenated by an oxygenator, and a heat exchanger. A heat exchanger is constructed around the perfusate reservoir. In one embodiment, the bottom portion of the organ chamber containing the perfusate reservoir and head exchanger is constructed from a transparent material that can be autoclave sterilized, and is the same material as the top portion or lid of the organ chamber.

The oxygenator comprises of a platform resting atop at least three support members. The support members of the platform contain comb-like ridges around which tubes carrying oxygen can be wound. In one embodiment, oxygenator tubes are made from flexible, gas permeable, autoclavable material that sufficiently allow for oxygen diffusion through the membrane of the tube into the perfusate. The diffusion of oxygen from the tube oxygenates the perfusate. A pressure gage and flow meter are connected to the oxygenator tubes to ensure oxygen flows through the tubes at the appropriate rate and pressure.

A magnetic stirrer, is located at the bottom of the organ chamber, and activated by a rotating magnet enclosed in the base, beneath the organ chamber.

Temperature controlled perfusate is pumped through a bubble trap before it is introduced to the organ. Temperature and pressure sensing devices are used to ensure perfusate is delivered to the organ at the desired parameters.

Signals from the temperature and pressure sensors are transmitted to the control section and displayed. The control section contains an ON/OFF switch and a momentary switch which allows the pressure to reset to zero. The control section also contains a knob or other user input device for the user to select the desired flow rate of the pump.

Numerous other advantages and features of the present invention will be become readily apparent from the following detailed description of the invention and the embodiments thereof, from the claims and from the accompanying drawings.

DETAILED DESCRIPTION OF THE PREFERRED EMBODIMENTS

Figure 1:
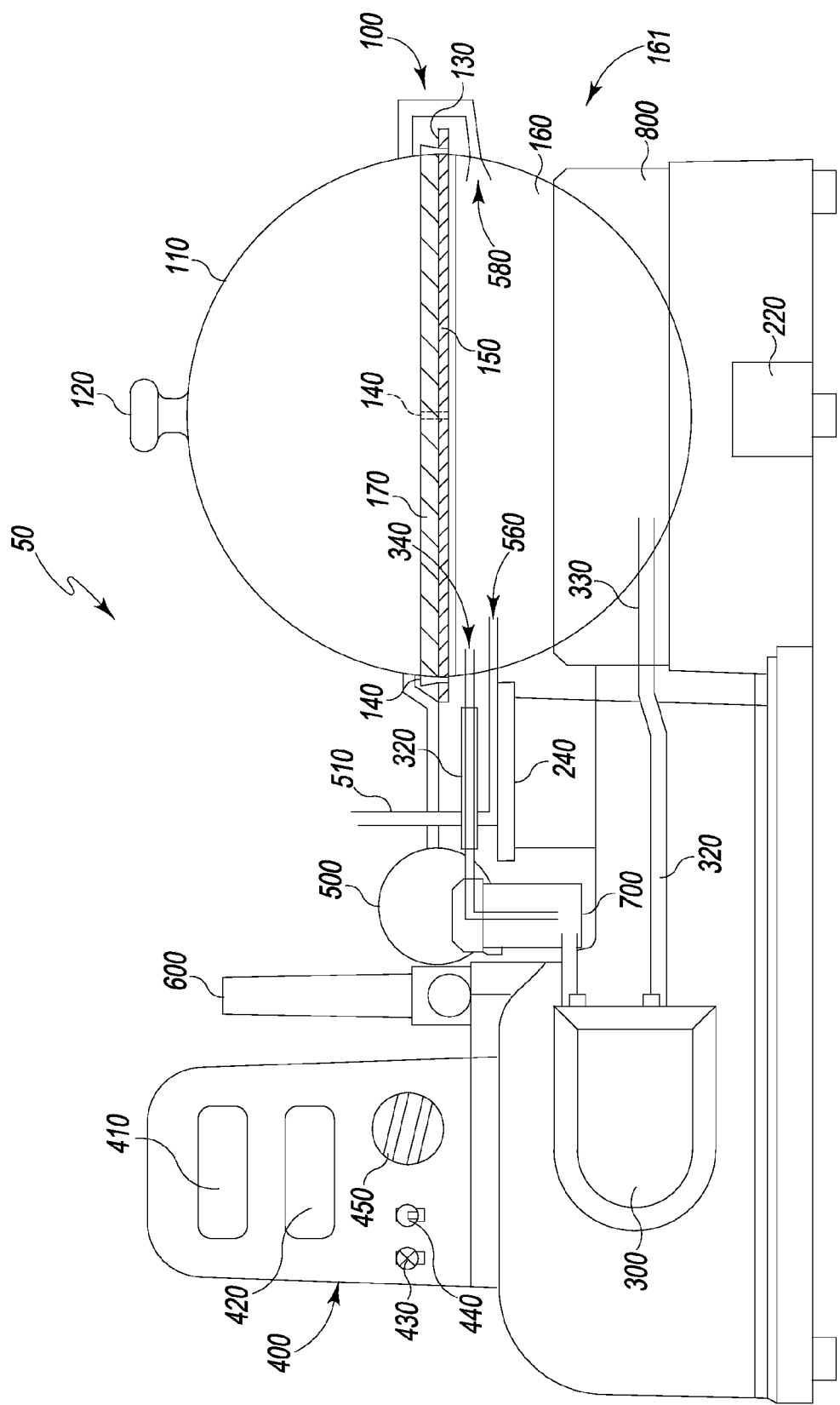
FIG. 1 is a front view of the organ preservation system of an exemplary embodiment of the invention.

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

FIG. 1 illustrates the various components of the organ preservation system 50. The organ preservation system 50 comprises a chamber section 100, a heat exchanger 800, a base section 200, a pump 300, a control section 400, and a bubble trap 700.

Chamber Section

FIG. 1 illustrates a chamber section 100 suitable for use with a kidney. The chamber section is generally spherical on both ends. The chamber section has a top portion which comprises a lid 110 and a handle 120. In another embodiment, the chamber can have a cylindrical shape where either the top portion, bottom portion or both are spherical. The top portion of the chamber can also be an elliptical shape or another shape with a higher dome to accommodate a larger organ such as a heart, liver, or lung.

The lid 110 is made of transparent, rigid material that can be autoclave sterilized. Suitable materials include various types of glass, but preferably borosilicate glass. The chamber section is formed with glass of an appropriate thickness to allow for adequate support of the weight of the lid and handle, as well as adequate thickness to allow for insulation to prevent the internal temperature of the chamber from being affected by external conditions.

Figure 6:
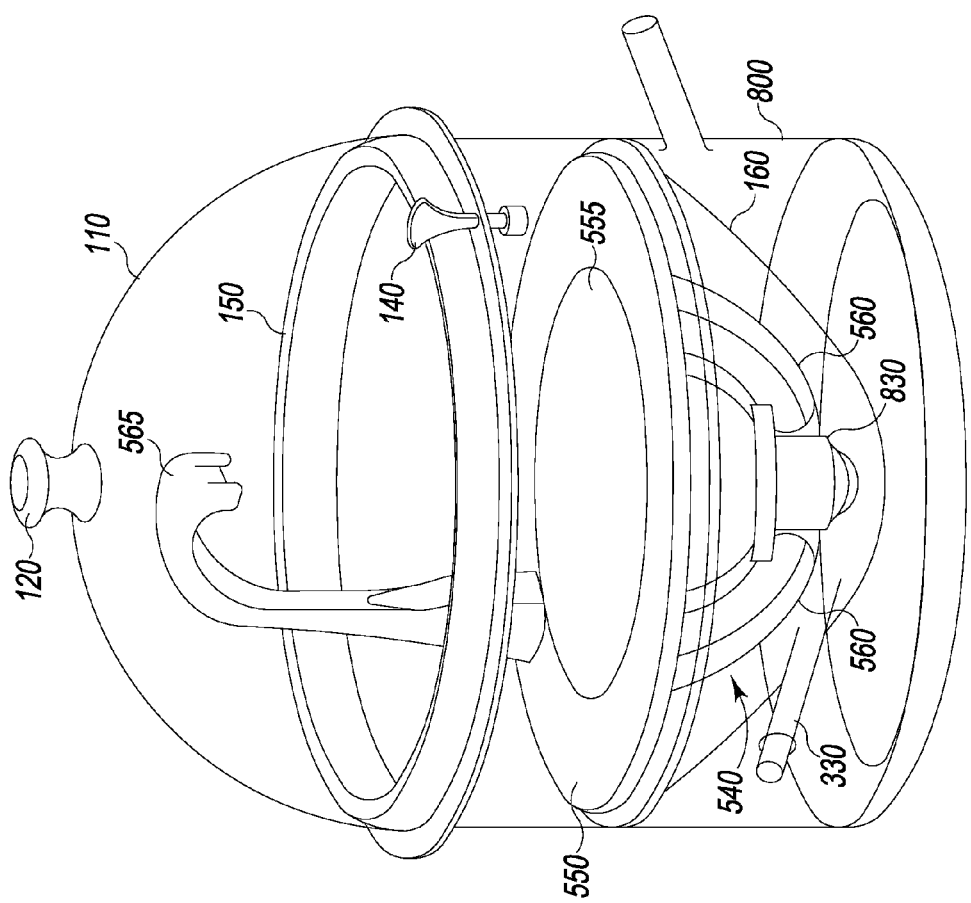
FIG. 6 is a perspective view of the chamber section.
Figure 7:
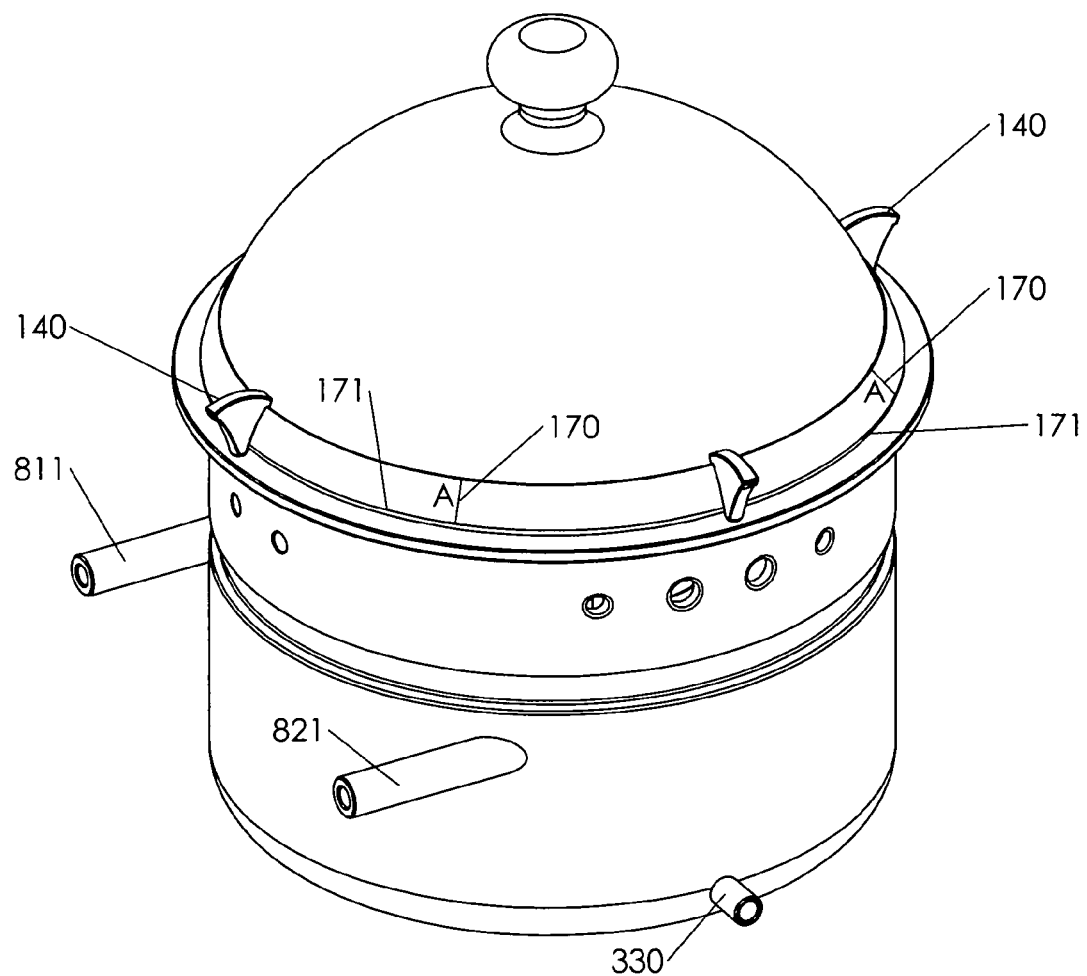
FIG. 7 is a perspective view of an empty chamber section.

A handle portion 120 is on top of the lid or formed in the top portion of the lid. The outer circumference 170 of the lid is frosted to allow for better contact between the lid 110 and a fastening clip 140 as shown in FIG. 7. The frosted outer circumference extends from the inner edge of the lip 171 towards the top of the lid a distance A, such that distance A is approximately the height of the fastening clip 140. The fastening clip is attached to the outside of the lid and holds the lid against the bottom portion of the chamber. A ring-shaped seal 150, as illustrated in FIG. 6, can be placed around the inner circumference of the lid near where the top and bottom portions of the chamber come together to maintain the integrity of the chamber environment. The frosted outer circumference 170 is not shown in FIG. 6. The seal 150 can be made of rubber, silicone, plastic or other synthetic materials. The seal is made from silicone plastic.

Figure 2:
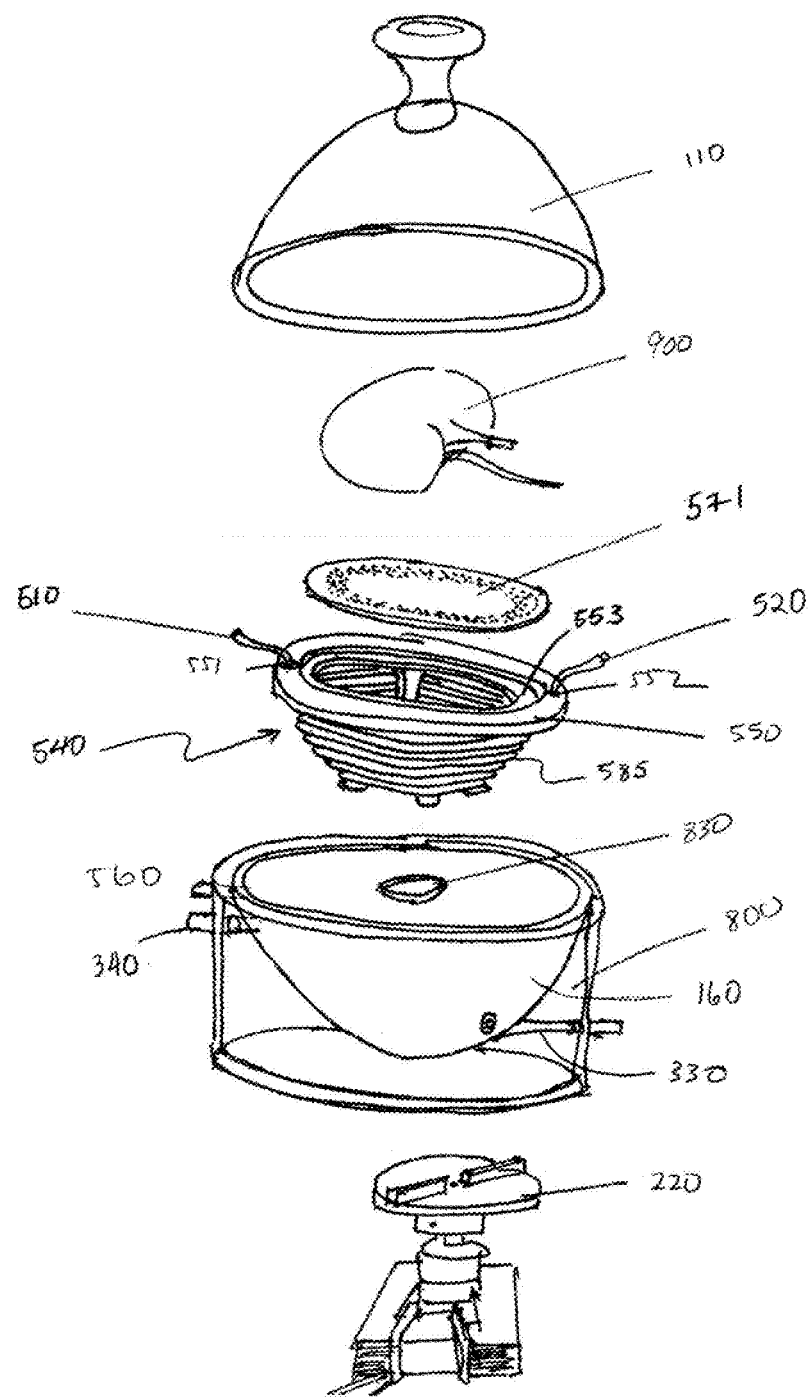
FIG. 2 is an exploded view of the chamber section of an exemplary embodiment of the invention.

FIGS. 2 and 6 illustrates the various components of the organ chamber. The bottom portion of the organ chamber contains a perfusate reservoir 160 where the perfusate is oxygenated by an oxygenator 540, and a heat exchanger 800 to maintain the perfusate at desired temperatures. The bottom of the perfusate reservoir 160 is nested within the heat exchanger 800 such that fluid in the heat exchanger comes in contact with the surface of the perfusate reservoir.

The bottom portion 161 of the organ chamber containing the perfusate reservoir 160 and heat exchanger 800 is preferably constructed from a transparent material that can be autoclave sterilized, and is preferably the same material as the top portion, or lid, of the organ chamber. The perfusate reservoir and the heat exchanger can be formed as separate portions then joined together, or can be formed as one continuous unit. In operation, the level of perfusate in the perfusate reservoir 160 should be sufficient to minimize splashing of the perfusate as it drips back into the perfusate reservoir to be collected and oxygenated. In one embodiment, the perfusate spreads out on the oxygenator platform 550 and a filter 571 until it reaches the sides of the chamber, wherein the perfusate flows down the side of the chamber to minimize dripping or splashing.

Figure 4:
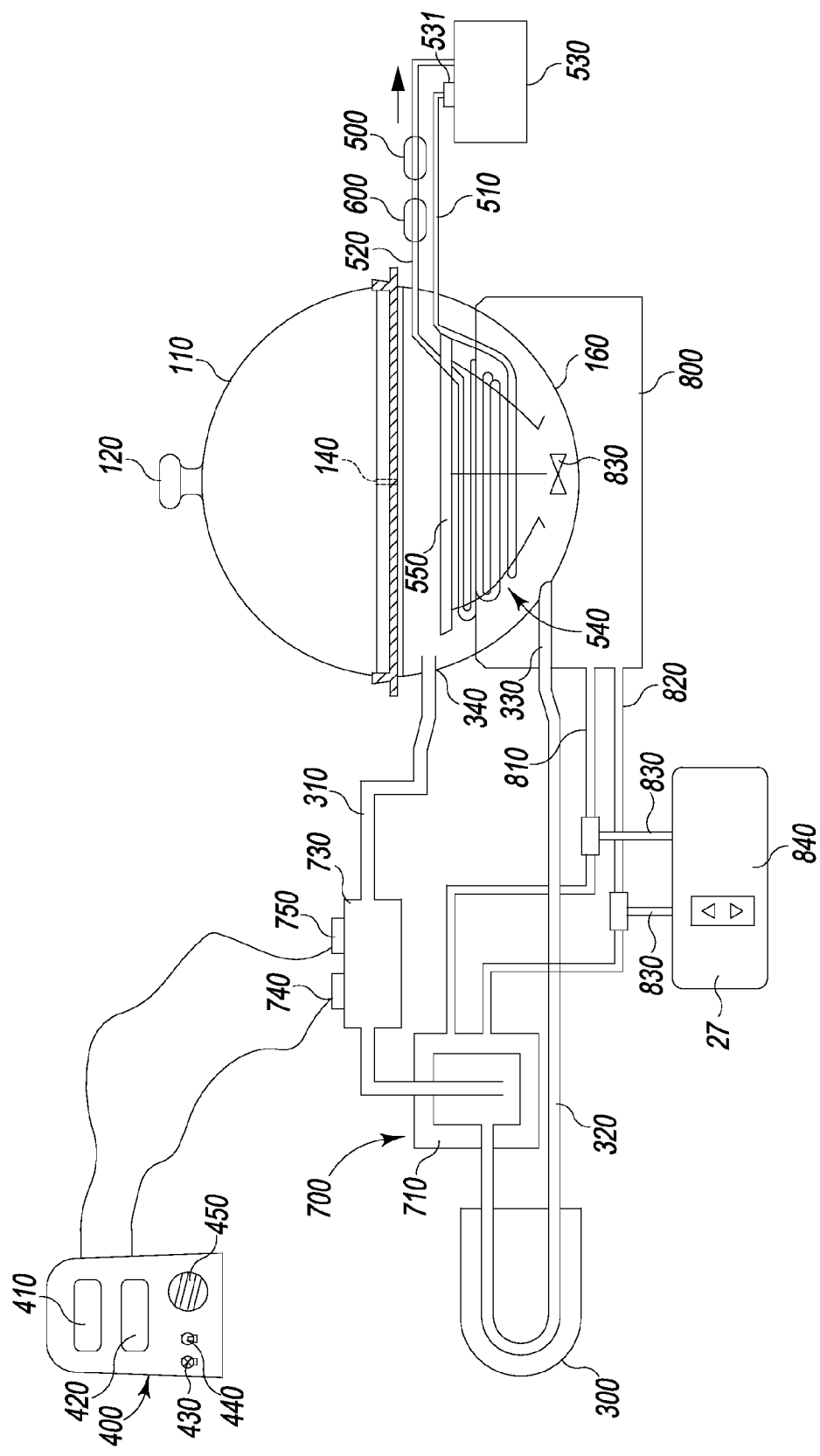
FIG. 4 is a schematic diagram illustrating the fluid flow pathways of the organ preservation system.
Figure 5:
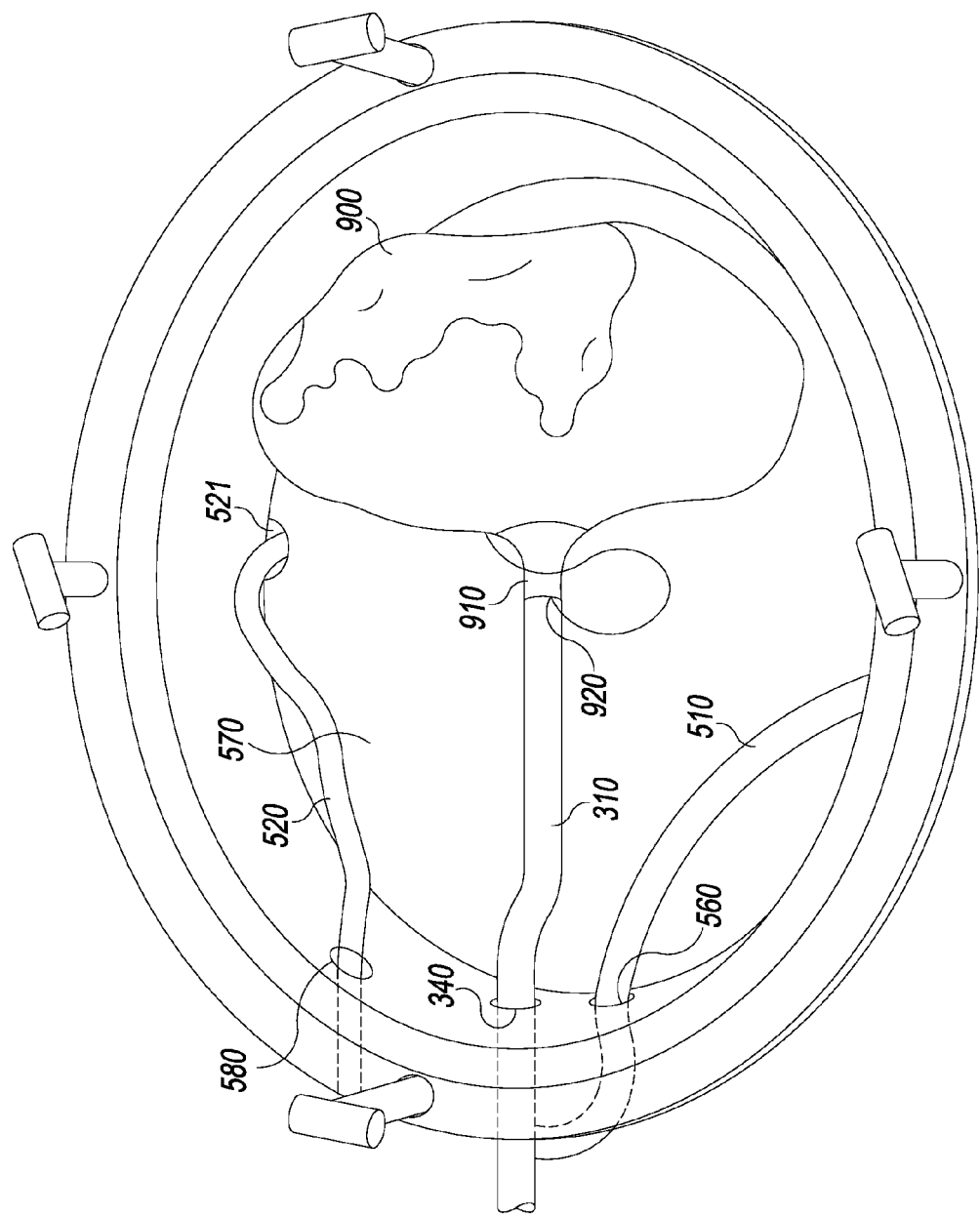
FIG. 5 is a perspective view of the organ chamber in use with a kidney and having parts not shown for clarity.

FIG. 5 illustrates a perfusate inlet channel 340, an oxygen supply inlet channel 560, and an outlet channel 580 for the oxygen supply situated above the perfusate reservoir 160 which can either enter though the heat exchanger as shown in FIG. 2, or through a portion of the bottom chamber not nested in the heat exchanger 800, as illustrated in FIGS. 1 and 5, depending on the configuration of the chamber. As illustrated in FIGS. 1, 2, 4, 6, and 7, a perfusate outlet channel 330 is connected to the perfusate reservoir 160 at a bottom portion of the reservoir 160 and is connected at an opposite end with tubing, to the pump. The channel 330 extends through the heat exchanger 800 between the reservoir and the pump. In FIG. 7, two heat exchanger flow channels which serves as an inlet flow channel 810 and an outlet flow channel 820 extend from the back of the heat exchanger so that fluid, usually water, from an external source can be introduced, and circulated through the heat exchanger 800 to provide temperature regulation.

Oxygenator

Figure 3:
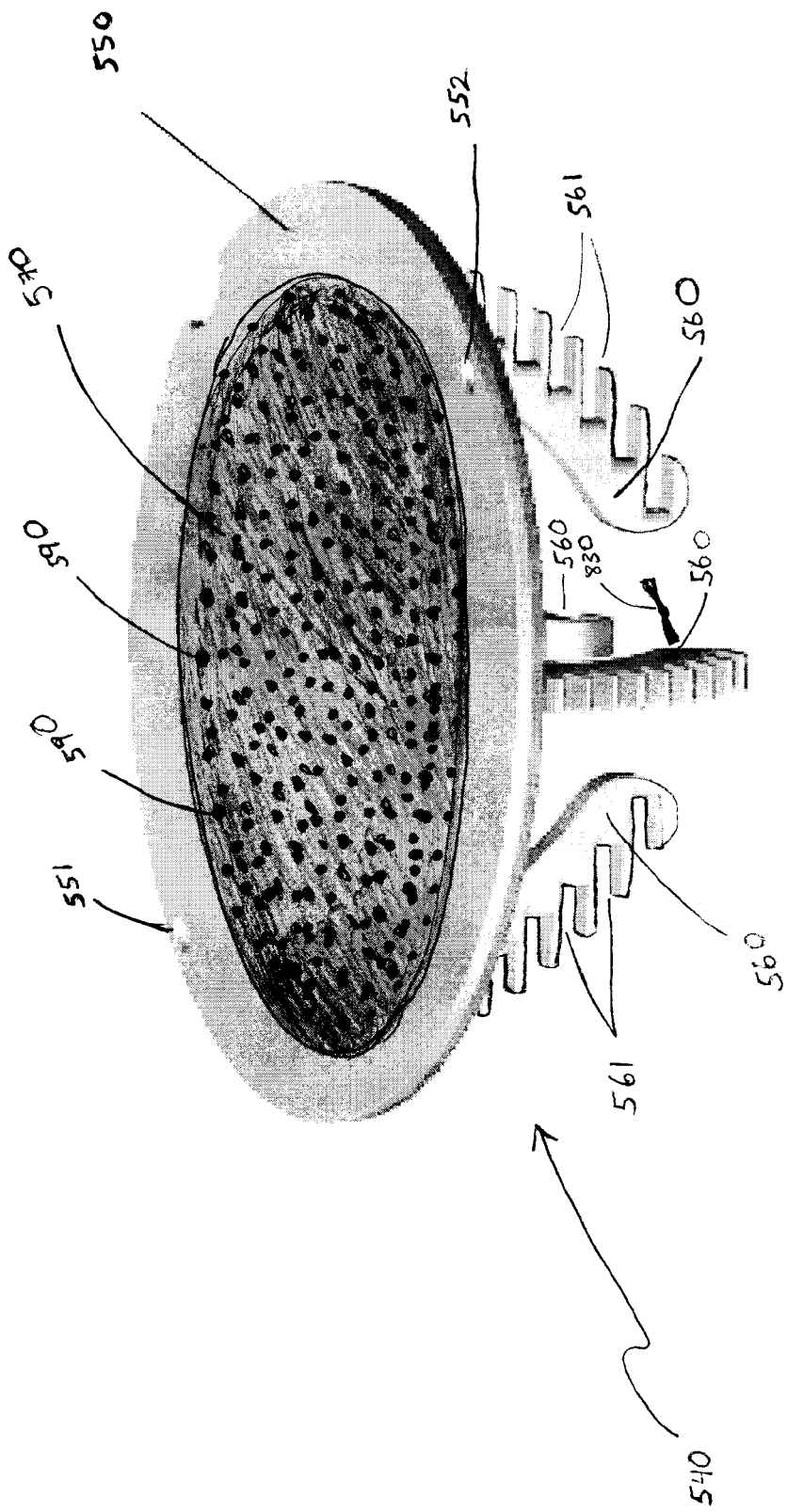
FIG. 3 is a perspective view of the oxygenator.

FIG. 3 illustrates the oxygenator 540 comprising a platform 550 connected to at least three support members 560. The support members 560 of the platform contain comb-like slots 561 around which tubes carrying oxygen 585 are wound. FIG. 2 illustrates the winding of the oxygen tubes 585 around the support members. The comb-like slots 561 maintain spacing around the oxygenator tubes 585 to allow for perfusate to flow around the tubes. Comb slots are of necessary depth to allow multiple windings of specified count to achieve the desired gas transport surface area.

The support member legs 560 are curved to allow circular windings consistent with the general shape of the perfusion reservoir, and are spaced sufficiently apart from each other to provide clearance and accommodation for the rotating stirrer 830. The support members 560 are adjustable such that various tubing diameters and lengths can be used.

As illustrated in FIG. 2, the oxygenator platform 550 is ring shaped with a recessed inner edge 553 of the ring to allow for a filter 571 to be inset into the recess. The filter 571 can be disposable and replaced, or removed and sterilized for reuse. The organ is placed on the filter 571. Perfusate exiting the organ passes through the filter 571 prior to being rejoined with the perfusate in the perfusate reservoir 160 below. As illustrated in FIG. 3, the filter openings 590 are preferably situated over the oxygenator tubes 585 to allow for perfusate drip directly onto the oxygenator below.

The filter 570 is preferably made from rigid material that can withstand autoclave sterilization, such as 300 Series stainless steel. As shown in FIGS. 2 and 3, the filter is disc shaped. In other embodiments, the filter may be cone or parabolic shaped to accommodate the different organs, such as for example, the apex of the heart. Alternatively, in some embodiments, the filter 571 may comprise of a ring of filter openings as illustrated in FIG. 2, positioned close to the perimeter of the oxygenator to allow for perfusate to spread closer to the edge of the platform before dripping down. In one embodiment, the filter may be intermittent throughout the surface of the platform, or comprising several concentric rings. In another embodiment, the oxygenator platform may be two tiered, such that perfusate dripping through the filter 570 as shown in FIG. 3 drips down to a platform below (not shown) that allows the filtered perfusate to spread to the edge of the organ chamber and drip along the walls of the organ chamber so as to minimize perfusate splashing or dripping. One skilled in the art would understand that various filter configurations are available.

The platform 550 includes at least two holes 551, 552 in the ring to allow for oxygen tubes to be inserted through and wound around the support members 560. Oxygen supply tube 510 is inserted through a hole 551 in the platform 550 and is wound between the comb slots 561 around the tube holders 560. After the tube has been wound into the comb slots, it is inserted through hole 552 and directed above platform 550 to become oxygen exit tube 520. Oxygenator tubes are preferably made from flexible autoclavable material that sufficiently allows for oxygen diffusion through the membrane of the tube into the perfusate. The diffusion of oxygen from the tube oxygenates the perfusate.

Oxygen is supplied to the oxygenator via an oxygen supply source such as an external oxygen tank 530. The oxygen supply is metered by a regulator 531. A pressure gage 500 and flow meter 600 are connected respectively to the oxygenator tube 520 to measure the oxygen pressure and flow rate upon exit from the oxygenator. In some embodiments, the oxygen flow rate can be adjusted using the flow meter.

The perfusate is oxygenated as it circulates around the oxygenator tubings 585. Oxygen is transported to the perfusate by diffusion from the surface of tubing in the oxygenator. The tubing is made of a flexible material that is gas permeable, but not water permeable. Suitable tubing includes silicone tubing, such as that made from Silastic™, or other materials. For example, polyethylene tubing may also be used.

A magnetic stirrer 830 situated inside and at the bottom of the perfusate reservoir 160 creates a convective current in the perfusate to circulate the perfusate around the oxygenator. The current in the perfusate also helps to equilibrate the temperature of the perfusate. The stirrer 830 in the reservoir is rotated by magnetic coupling to a motor-driven magnet 220 enclosed in the base.

As one in skilled in the art would appreciate, generating operating conditions for the oxygenator requires taking into consideration a variety of factors, including organ type and perfusate temperature. An organ of a larger size and higher metabolic rate would require more oxygen than an organ of a smaller size and lower metabolic rate. Operating temperature also affects the diffusion and oxygen pressure in the perfusate. Based on these factors, the oxygenator is sized and ideal operating conditions are established. For example, silicone tubing with 0.8 mm thickness for a 50 gram kidney needing an estimated 1.5 mL/min of $O_2$ with a desired perfusion temperature of 27° C. using RS-I as perfusate would require an oxygen pressure of 760 mmHg absolute, an oxygen flow rate of 0.5 L/min, and a rated transport of 3.7 mL/min.

Oxygen delivery can be increased by proportionately increasing the oxygen pressure, increasing the surface area, and decreasing the wall thickness of the oxygenator tubes, as well as increasing the stirrer-turbulence. Oxygen delivery can be reduced by proportionately decreasing oxygen pressure and surface area, and increasing the wall thickness of the oxygenator tubes.

Heat Exchanger

As illustrated in FIG. 4, temperature control of the perfusate and organ is provided by a re-circulating heating and cooling system 840 which directs temperature-controlled fluid to a heat exchanger 800 via channels 810, 820. In one embodiment temperature-controlled fluid is also circulated around an outer jacket 710 of the bubble trap 700 as illustrated in FIG. 4. The temperature of the fluid can be set by temperature buttons 27 on the heating or cooling system 840; or alternatively can be computer controlled via a temperature interface (not shown) on the control section 400. Other embodiments for temperature control include direct contact cooling, heat pipes, thermoelectric Peltier devices, and other common approaches. The temperature controlled fluid can be water, antifreeze, or other suitable fluid.

FIGS. 1, 2, 4, and 6 illustrate the heat exchanger 800 enclosing around, and surrounding the bottom portion of the perfusion reservoir 160. The heat exchanger is preferably made from the same material as the bottom portion of the chamber. The heat exchanger comprises two channels 811, 821, illustrated in FIG. 7, serving as fluid inlet and outlet which circulate the heating or cooling fluid, and are respectively connected to tubes 810, 820 which carry the heat exchanging fluid. The outlet 330 from the perfusion reservoir extends through the heat exchanger. Preferably, the perfusate in the reservoir is equilibrated to the desired temperature prior to perfusing.

Base Section

The base section 200, as illustrated in FIG. 1, provides support for the various components of the organ preservation system. A stirring magnet 220 is enclosed within the base, below the perfusion reservoir 160, to transmit a rotating magnetic field to the stirrer 830. Rotational speed is about 100 to 600 revolutions per minute and may be held at a fixed speed or may be adjusted by the user as needed.

A pump 300 which is used to regulate the delivery of the perfusate at the right pressure is attached to the base. The base supports a table 240 on which tubes carrying perfusate 310 and oxygen 510 into the organ chamber rests. A control section 400, bubble trap 700, pressure gage 500 and flow gage 600 are also attached to the base.

Pump

The pump 300, as illustrated in FIGS. 1 and 4, regulates the delivery of the perfusate into the organ via a perfusion circuit The perfusion circuit comprises of the perfusate leaving the pump and entering a bubble trap 700 to remove air bubbles. The perfusate then passes through a manifold 730 to which a temperature sensor 740 and a pressure sensor 750 are connected. The perfusate flows out from the manifold to enter the organ chamber via the perfusate inlet channel 340. Tubing connects the perfusate inlet channel to a cannula attached to the organ to allow perfusate to flow into the organ. Upon exit from the organ, the perfusate drips into the perfusion reservoir 160 below, and exits the reservoir via the perfusion outlet channel 330, to be returned to the pump 300.

In one embodiment, the pump is a peristaltic pump which uses the action of rollers against a flexible tube to move the perfusate from reservoir to organ. The peristaltic pump type configuration allows for the separation of the machinery from the sterile tube containing the perfusate. In alternative embodiments, other pumping configurations such as a centrifugal pump with autoclave sterilizable parts may be used. Preferably, the pump is a peristaltic pump.

Bubble Trap

As illustrated in FIG. 4, the bubble trap 700 is situated downstream from the perfusate flow exiting the pump, and ensures that the perfusate flowing into the organ is free of bubbles. The bubble trap preferably is surrounded by an insulating jacket 710 to maintain desired temperature consistency. The insulating jacket can be connected to the same or different circulation as the heat exchanger, but is preferably connected to the same circulation. Once the perfusate passes through the bubble trap, it enters a manifold 730 where the perfusate comes in contact with a temperature sensor 740 and a pressure sensor 750 as illustrated in FIG. 4.

Control Section

The control section 400 is situated on the base. The control section provides a user interface which comprises ON/OFF switches 430, 440, a temperature display 410 and pressure display 420, and a knob 450. In one embodiment, the control section has two switches, an ON/OFF switch 430 and a momentary switch 440 to re-zero the perfusate. The knob 450 is adjusted by the user to select the desired flow rate of the pump 300. Signals from the pressure sensor 750 and the temperature sensor 740 are transmitted to the pressure display 410, and the temperature display 420 respectively. The pump 300 can also be controlled by regulating the pump revolutions per minute, pressure, waveform, frequency, duty cycle, and amplitude of selectable pulsatile output. A tachometer (not shown) can be used to measure RPM. In other embodiments, ultrasonic or other means of directly measuring flow rate can be used as a way to collect input for the user to be displayed in the control section. In other embodiments, the control section can house additional user interfaces for control of additional perfusate parameters.

Perfusate

The perfusate as described herein is a fluid or slurry that is directed through the blood vessels of the organ. The perfusate may be blood, a blood derivative, a synthetic perfusate, or a combination thereof. The perfusate performs some of the functions of blood such as supplying the organ with oxygen and glucose, and removing waste products such as carbon dioxide and lactate. As one skilled in the art would appreciate, the function of blood in an organ is complex and multifaceted, and perfusate should be understood to encompass any or all of the blood function.

Where the perfusate is blood, an anti-coagulant such as heparin is usually used to prevent clotting. The blood is preferably from the same source as the donor organ to prevent rejection or inflammation, or at least of the same blood type from the same species.

The perfusate may also be a blood derivative. The perfusate may be the acellular or serum component of the blood comprising water, electrolytes, sugars, and other chemicals needed to support the organ. This type of serum perfusate can be used when perfusing an organ at temperatures about 25° C. or below, as there is sufficient solubility of oxygen in water to support the organ without needing red blood cells. Serum based perfusate can be derived from the same donor as the organ, or at least from the same blood type from the same species to avoid rejection and inflammation.

The perfusate may also be synthetic with chemical composition similar to blood serum. Examples of suitable synthetic perfusates include various cell culture media such as Krebs-Henseleit solution, which is available for example, from Sigma-Aldrich, Inc., or organ preservation media such as Aqix® RS-1 solution or Steen Solution™ available from Vitrolife, Inc. Alternatively, the perfusate chemical composition may be more similar to the cytoplasm. Examples of cytoplasm-like perfusate include ViaSpan® sold by Barr Laboratories, Inc. Other organ preservation solutions may also be perfusates including KPS-1® from Organ Recovery Systems, and Perfadex® from Vitrolife, Inc.

Synthetic perfusate may be mixed with natural components such as albumin for oncotic support or washed erythrocytes or hemoglobin for oxygen capacity. In other embodiments, artificial components to increase the oxygen carrying capacity of the perfusate, such as perflourocarbons, may be added to the perfusate. The perfusate may also contain antioxidants to reduce tissue damage and enhance tissue protection. Examples of other additives which can be used in perfusion solutions are disclosed in U.S. Pat. No. 6,046,046, the entire disclosure of which is incorporated by reference. Other suitable materials for perfusion solutions as known by one skilled in the art, may be used.

Where rapid cooling of the organ is desired to prevent ischemic damage, perfusates may be formulated as ice slurries in the manner disclosed by U.S. Pat. Nos. 6,962,601 and 6,547,811, or formulated with other methods known to one skilled in the art. U.S. Pat. Nos. 6,962,601 and 6,547,811 are incorporated by reference.

The delivery of the perfusate to the organ via the system may be continuous or non-time varying, or pulsatile. Pulsatile pressure mimics the physiological environment, and allows for the delivery of a relatively higher peak pressure to open capillaries and activate pulse-sensitive endothelial function in the cells, but at a lower relative average pressure which reduces barotrauma to the endothelium and reduces pressure-related edema or swelling or water accumulation between and inside the cells.

Pulsatile pressure using a pressure waveform bounded by a high and low pressure, systolic and diastolic, respectively, is delivered with consistent timing. Systolic pressure of 60 mmHg and diastolic pressure of 40 mmHg may be delivered at a rate of 60 beats per minute. Other pulsatile pressure embodiments would entail other pulse rates ranging from 4 beats per minute to 200 beats per minute, and systolic pressures at 200 mmHg and above.

Other methods of pressure programming are described in U.S. Pat. Nos. 6,027,498 and 5,941,841, which are each incorporated by reference. These methods describe delivery of varied pulse pressure to mimic natural pulse pressure variation in vivo. In U.S. Pat. Nos. 6,027,498 and 5,941,841, pulsatile programming can be derived from recording actual heart and lung pulse variability and then simulating the variability. Variable pulse pressure can be used in conjunction with aspects of the present invention. Other methods of variable pulse pressure generation include synthetic variation of pulse pressure by application of stochastic variation by a predetermined distribution including random distribution, normal distribution, and power law distribution whose parameters are set to bound high and low limits as determined by the design. For example, systolic pressure could be controlled to vary randomly between 70 mmHg and 50 mmHg when the user sets the average pressure at 60 mmHg. Likewise, pulse rate could be set to vary randomly between 40 and 60 beats per minute. In these examples, duty cycle of the pulses is 50%, although other duty cycles can be applied.

Short duration-elevated pressure pulses followed by extended inter-pulse time can be used to deliver increased peak pressure while maintaining low average pressure. For example, 200 mmHg peak pressure is applied for 100 ms followed by 900 ms while the pump is held off. This equates to an average pressure of 20 mmHg at 10% duty cycle. Such a pulse pattern would reduce the possibility for edema by holding low the average pressure while opening the capillary bed by increasing the peak pressure. These effects of lower edema and open capillaries increase the probability of proper organ function after transplant. Other duty cycles and peak pressures and pulse timings are intended to be covered within the scope of this description Any of the above mentioned pulse pressure profiles may be used in combination in the system. For example, a short duration-elevated pressure pulse may be used in combination with a natural variability pulse, or a synthetic variability pulse.

During perfusion, additional preservation strategies may be employed to effect changes in the organ, mostly to improve function on transplant. Perfusion can be performed at mild to moderate hypothermia (25° C. to 36° C.) to enable increased metabolic activity, for example, in the kidney, and increased opportunity for self-repair and homeostasis. Perfusion at deep to profound hypothermia (2° C. to 10° C.) can be performed to enable metabolic arrest and increase preservation duration with minimal change or damage to the organ.

Provision of various materials and conditions beneficial to viability of the organ can be accomplished during perfusion. For example, providing antioxidants such as reduced glutathione compounds and superoxide dismutase, flushing of blood from the capillaries and removing or binding of free electron-carrying metals, can block the consequences of ischemia, including ischemia reperfusion injury, and encourage ischemic repair. Provision of vaso-relaxants such as nitric oxide or provision of varying pressure perfusion can reduce vascular resistance and increase perfusion through the capillaries of the organ. Providing ATP and its components including adenosine, alternate pathway substrates such as pyruvate or cyclocreatine, glycolytic intermediates such as 1,6 fructose-bis-phosphate, sugars such as glucose or mannose, and sugar transport activating molecules such as insulin allows the organ to increase its energy stores and preconditions the organ toward immediate function on transplantation. The perfusate can also be used to provide proteins to decrease apoptosis of cells before and after transplant. For example, proteins that block intracellular caspases and kinases associated with apoptosis, or proteins that block extracellular signals as might be transduced for example by the toll-like receptor can be included in the perfusate to enhance organ viability.

The perfusion circuit can also be used to decrease the inflammatory and rejection responses after transplantation by elution and capture, or inactivation of passenger leukocytes and dendritic cells. Perfusion also provides means for example to reduce the expression of major histocompatibility complex molecules on cell membranes, to bind competitively to cell membranes receptor or second signal molecules for example by antibodies, to inhibit endothelial activation and the complement cascade, and to preferentially increase the expression of regulatory and anti-inflammatory cytokines such as interleukin-10. Furthermore, anti-inflammatory medicines such as anti-TNF (Embrel) and anti-rejection medicines such as anti-thymocyte globulin (Thymocyte) or other such medicines and antibodies may be applied during preservation to reduce rejection during transplantation. This may be especially helpful in transplanting organs after long periods of ischemia, or into blood-type mismatch or xenogeneic (animal-to-human) transplantation. Perfusion during organ preservation can also be used to reduce coagulopathy in the patient after transplantation. Hypertonic perfusate solutions can be used in the manner practiced in trauma medicine to reduce edema and re-establish vascular patency. Finally, perfusate solution can be used to deliver RNA interference to block pro-inflammatory protein expression.

The surfaces of the system 50 coming in contact with perfusate must be biocompatible when used for organs with human clinical uses. A surface is considered to be biocompatible for this apparatus if it is non toxic when placed in direct blood contact for 24 hours, or adheres to other standards set forth by the Food and Drug Administration, or other relevant heath administrative authority. Surfaces coming in contact with perfusate can be sterilized using an autoclave, or other sterilization methods including ethylene oxide gas sterilization, electron beam and gamma radiation sterilization. Alternatively, certain parts that come into contact with the perfusate can be designed as single-use sterile components.

Perfusate-contacting components and example materials are provided in Table 1. The perfusate-contacting components in Table 1 are biocompatible, and can all be sterilized. The fastening is pre-sterilized.

TABLE 1

Perfusate-contacting parts in one embodiment of the system.

| Number | Name | Contacting Material | Manufacturer |
|---|---|---|---|
| 100 | chamber | borosilicate glass | Functional Circulation |
| 110 | lid | borosilicate glass | Functional Circulation |
| 540 | oxygenator | PVDF plastic | Functional Circulation |
| 560 | tube holder | PVDF plastic | Functional Circulation |
| 585 | tube | silicone plastic | Cole Parmer |
| 700 | bubble trap | borosilicate class | Functional Circulation |
| 310 | tube | silicone plastic | Cole Parmer |
| 150 | seal | silicone plastic | Functional Circulation |
| 910 | cannula | PVDF plastic | Value Plastics |
| 920 | fastening | silk (presterilized) | Ethicon |
| 510 | oxygen supply | silicone plastic | Cole Parmer |
| 520 | oxygen exit | silicone plastic | Cole Parmer |
| 740 | temperature sensor | 300 series stainless | Omega Engineering |
| 750 | pressure sensor | 300 series stainless | Transducers Direct |
| 730 | manifold | PVDF plastic | Functional Circulation |
| 830 | Stirrer | PTFE plastic | Cole Parmer |
| 570 | filter | 300 series stainless | Functional Circulation |

In the embodiment illustrated in FIG. 5, the organ rests on a platform 570. The organ, shown as a kidney, is perfused through the artery using a cannula 910 which is secured in place by a fastening 920. The perfusate exiting the vein (not shown) of the organ is returned by gravity to the perfusate reservoir below. Inlet channels 340, 560 allow tubing for the perfusate 310, and tubing for oxygen supply 510, respectively, to be inserted into the chamber. Outbound oxygen from the chamber is carried by tube 520 which is passed up through a hole 521 in the platform after being wound around the oxygenator below. The outbound oxygen tube 520 passes through outlet 580 from the chamber. The organ platform 570 and the perfusate reservoir is preferably situated such that the platform is not too high above the perfusate surface so as to minimize any splashing or foaming caused by dripping perfusate.

Perfusate Sampling

In one embodiment, the perfusion circuit can include an outlet to collect samples of the perfusate for further testing. Perfusate sampling is accomplished by inserting a valve at a point in the perfusion circuit along perfusion outbound tube 320 in FIG. 1, and removing a sample of perfusate. It can be appreciated that other suitable locations for perfusate sampling, such as at the point of exit from the vein, can be used. The sample can be returned to the perfusate circuit if desired.

In other embodiments, various sensors may be used along the perfusate circuit to analyze, for example, gas levels in the perfusate, electrolytes present, glucose and lactate levels, and pH. Sensors for analysis of gas in the perfusate include use of a Clark electrode, or absorption oximetry. Analysis of electrolytes can be performed, for example, using ion selective electrodes. Measurements of glucose and lactate levels in the perfusate can be performed using electrochemical or spectrophotometric analysis. The pH of the perfusate can be measured with a pH electrode. Identification of the presence of target proteins in the perfusate can be accomplished by performing binding assays or ELISA on the perfusate.

Signals from perfusate sampling sensors may be displayed on gauges, may be processed, stored, placed onto interfacing connectors for external analysis, or used internally for servo control. Servo control may include adjusting flow rate in coordination with pressure, adjusting oxygen flow or gas mixture in response to blood gas, dispensing drugs or chemicals into the perfusate in response to measurements of expressed proteins or other measurements. The engineering aspects of servo control are well developed in the art.

In addition to the use of sensors, perfusate may be collected from an effluent receptacle or from other locations for off-line analysis. Offline analysis may include blood chemistry, urinalysis, and panels and assays for liver enzymes, creatinine, malondialdehyde, lactate dehydrogenase, caspases, interleukins, white blood cells counts, types and status, platelets and activation states, hematocrit, heart enzymes, plus dosing and response to agents and other conditions of interest.

Effluent Collection

In the process of kidney perfusion, for example, urine-like filtrate is produced by the kidney. Filtrate leaves the ureter of the kidney into the excretory duct where a tube (not shown) may be connected to collect the effluent into an effluent receptacle (not shown). Such collection of the effluent allows for the analysis of the organ and related biomarkers to assess the condition of the organ.

Perfusion of Other Organs and Tissues

The organ preservation system 50 is suitable for use by various organs and tissues, transplantable and non-transplantable, including liver, heart, pancreas, lungs, small intestine, skin, limbs, thymus, islets, hepatocytes, and cells in culture, for transplantation preservation or medical research purposes. These organs and other structures are generally the same as those described previously for the kidney. As one skilled in the art will recognize, every organ or tissue has an artery or arteries from which the perfusate can enter, and veins from which the majority of perfusate leaves the organ. Examples of certain uses that are specifically applicable to organs besides the kidney which has been discussed above, are described below.

In one embodiment used for preservation of the heart, an opening 555 in the platform may be made such as to enable the entire heart, or a portion of it, to pass thorough the platform, as illustrated in FIG. 6. A tube containing inbound perfusate is hung from a gantry 565, as illustrated in FIG. 6, to allow perfusate to enter the aorta at the top of the heart and provide additional positional support. The gantry is preferably made from a rigid material that can be autoclave sterilized, such as PVDF plastic of the gantry manufactured from Functional Circulation. In another embodiment, supporting structures may be attached to the tube holders to position the heart at its apex and support the heart.

Perfusion of the pancreas requires perfusate flow to enter the splenic artery and superior mesenteric arteries. A fastening is applied where arteries passing through the pancreas exit to prevent perfusate leakage. Examples include applying the fastening where the splenic and superior mesenteric arteries flow out of the pancreas after the spleen is removed. Since the pressure requirements of pancreas arteries are approximately equal, they can be supplied by a single pump through tubes split by wyes and tees Effluent emits from the pancreas at the pancreatic duct into the duodenum. Cannulation of the duodenum will enable collection of pancreatic effluent. Fastenings applied to the openings of the duodenum will prevent the escape of pancreatic effluent and possible contamination of the perfusate.

In an embodiment for liver preservation, perfusion of the liver requires perfusate input from the hepatic portal vein and the hepatic artery. The pressure and flow requirements are different. The portal vein requires higher flow and lower pressure while the hepatic artery requires higher pressure and lower flow. For example at normothermia, a pig liver might require 1 liter per minute at 10 mmHg to its portal vein, and 100 mL per minute at 100 mmHg to its hepatic artery. In embodiments where the organ requires different perfusate flow and pressure at different input points, the system may comprise separate pumps with separate controls and pressure sensors to provide individually controlled perfusion to hepatic and portal vessels. Alternate pumping embodiments to support the liver include a single pump whose output is divided in a wye connection to supply both vessel systems. In another embodiment, stacked pump heads driven by a single motor whose flow rates would be in proportion to the cross section area of their respective peristaltic pump tubing. Another approach would use multi-lumen tubing in a single pump head, and flow rates would be in proportion to cross section area of the respective lumens. The chamber adapted for perfusion of the liver is of a sufficiently large size to contain the liver, and may include supporting structures to position the liver. Effluent, collected from the bile duct, can be analyzed for quantity and rate, and analyzed chemically using traditional and typical bile assays.

EXAMPLE 1

Example 1 provides one method of using the organ preservation system 50 to perfuse a porcine kidney at midthermic and normothermic conditions.

Upon excision from the physiological environment, the kidney is cannulated at the renal artery. One liter of blood is retrieved and collected in 1 L closed cap containers with heparin. The kidney is flushed with 100 ml of cold Krebs solution, and venous outflow is collected. Kidneys are maintained on ice, in RS-I solution (pH 7.4) during transport back to laboratory.

The organ preservation device is equilibrated at room temperature prior to perfusion, and RS-I perfusate is primed with oxygen at greater than 20 mg/dL. The kidney is placed in the organ chamber, on the platform. Perfusion is maintained at 60 mmHg continuous pressure, and between 15° C. to 25° C. perfusion temperature. The ureter is cannulated, and a tubing for filtrate is attached. The kidney is perfused for one hour.

During perfusion, the flow rate, pressure, temperature, $pO_2$, pH of perfusate is monitored. The filtrate is collected at 0 min, 15 min, 30 min, and 60 min to determine color, volume, and pH of the filtrate.

After perfusion of the kidney at midthermic conditions, the kidney is perfused at normothermic conditions. In preparation, the blood collected is cross matched with each kidney according to standard blood cross match protocols to identify best match blood.

The blood is pre-oxygenated by membrane diffusion as in the organ chamber. 500 mL best match blood is combined with 500 mL RS-I solution in the reactor, with the perfusate pH between 7.3 to 7.5. The heat exchange temperature is adjusted to a temperature of 37° C. Oxygen flow rate is adjusted to 200 ml/min at 10 PSI. The blood-RS-I perfusate solution is allowed to reach full oxygenation of greater than 20 mg/dL with the stirrer bar in operation.

Perfusion of the cold kidney is performed at a continuous pressure of 60 mmHg: Once perfusate temperature has reached 30° C., pressure is increased to 80 mmHg. The kidney is perfused at normothermic conditions for 1 hour.

During perfusion, the flow rate, pressure, temperature, $pO_2$, pH of perfusate is monitored. The filtrate is collected at 0 min, 15 min, 30 min, and 60 min to determine color, volume, and pH of the filtrate.

In other embodiments, the device may be connected to an organ donor to supply preservative fluid into the blood vessels of the donor, for example into the femoral artery via a cutdown and cannulation procedure. Effluent from the donor may be collected from the donor, for example from the femoral vein and oxygenated and temperature regulated in the apparatus, followed by recirculation into the donor.

In another embodiment, organs in the apparatus may be used as external-support organs for a living person by connecting the apparatus to a patient, via femoral artery and vein for example, and perfusing the organ with the patient's blood. In this embodiment, the patient receives the benefit of the organ, for example a liver for patients in acute liver failure, without requiring a full transplant. This allows a patient in need to maximize the use of an otherwise non-transplantable organ, for example one having insufficient functional capacity due to age or disease, or otherwise incompatible for long term transplant such as animal organs. For example, ex vivo application of the liver as a surrogate or short-term transplantation can also be achieved using the present invention.

The preservation of organs according to the system 50 allows for various processes to be carried out, such as conducting medical research or preconditioning or treating the organ.

The organ preservation system 50 can be used for research purposes such as gauging the metabolic response to certain agents and conditions of the liver in isolation. Recovery of the liver for possible transplantation following long ischemic times (greater than 11 hours), in non-heartbeating donation, in infected livers such as hepatitis C, and in fatty livers (steatosis) are examples of other uses for the organ preservation device.

The organ preservation system 50 can be used to precondition the organ. For example, a liver can be preconditioned in anticipation of hepatocyte transplantation. The organ preservation system, used to preserve a heart, can be used for extended preservation and preconditioning for immediate use. In the case of a pancreas, perfusion can be used to precondition the pancreas to improve the viability and yield of islets for islet transplantation. This might be accomplished by inhibiting the protease production of acinar cells to avoid protease interference with pancreas digestion in islet processing.

Other research uses for the organ preservation system include normothermic reanimation and testing via gas transport in ventilation of the lungs, as well as performing bioavailability studies to observe the transport of materials from the lumen of the intestine into the perfusate in the vasculature.

The organ preservation system can be used to develop new methods in organ preservation. Following preservation, the organ may be re-warmed to physiologic or near-physiologic conditions or temperature, pressure, flow, oxygenation, including possible inclusion of oxygen carrying molecules or cells as previously described. This re-warming procedure may be used as a surrogate or alternative for live transplantation, which provides a more economical endpoint plus providing an environment for direct observation and probing of the organ, and increased flexibility in possible perfusates and additives, as only the health of the organ needs to be preserved. This use of the isolated perfused organ can be applied economically to the evaluation of methods of organ preservation and develop confidence in approaches before undertaking clinical or preclinical trials. In another embodiment, perfusates and effluents may be collected and studied for the purpose of discovering and capturing biomarkers and performing probing experiments to test hypotheses in the translation of markers into diagnostic assays. Organ-blood interaction may be studied, for example to study inflammation and rejection as is experienced by transplanted islets in instant blood meditated inflammatory reaction (IBMIR) and the effects on survival and angiogenesis. Alternative studies in rejection mechanisms and possible approaches may be performed. For example, methods of blocking leukocyte adhesion and chemotaxis may be applied in the apparatus, evaluated, and possibly optimized.

Organ preservation can be used to provide an ex vivo viable organ for purposes of probing and measuring physiological pathways in the isolated organ. For example, the effects of drugs and agents may be evaluated directly on the target organ without the interference of other body systems. The organ preservation system would allow the user to study the ability of the kidney, for example, to excrete a particular molecule that is normally highly metabolized by the liver. Another example is the direct observation of the rennin and angiotensin pathways in regulating excretion and blood pressure. Classic pharmacokinetic studies of absorption, distribution, metabolism, excretion, and toxicity (ADMET) can be performed in the isolated organs and effects measured directly. This approach reduces the interference of other organs experienced in whole organism studies, while simulating the transport from blood to cell, which is not able to be studied in cells in culture.

Treatment methods can be evaluated using the organ preservation system 50. For example, the organ preservation system can be used to evaluate a kidney's functions to develop kidney-related therapies for acute organ failure, including traumatic shock-related kidney failure such as hypovolemic shock, or other kidney diseases such as hypertension and chronic kidney failure, or kidney transplantation.

Preservation of an organ ex vivo according to the embodiments of the organ perfusion device allows for studies of protein expression to be conducted. Genetic modifications to the organ through gene transfection, or other extracellular modifications to the organ such as stem cell or other cellular therapies may be delivered and evaluated in the apparatus and methods to change the organ response in the treatment of organ-specific diseases.

Ex vivo organ preservation according to some embodiments of the invention will allow imaging of the organs in the isolated state. Organs maybe imaged by imaging systems such as ultrasound, CT, PET/CT, SPECT, MRI. Such imagine can be used to gather data for evaluation of perfusion, energy status, functional activities, and structure of the organ, as well as to follow certain labeled markers and contrast agents as they are taken up and excreted. Using temperature adjustments, organs may be imaged safely in the arrested state, which is not feasible in vivo. Toxic or unverified contrast agents may be applied in certain isolated organs but may not be safe to the whole organism. In this sense, the apparatus and method enable novel imaging assays to be performed to test hypotheses and further develop the understanding of organ physiology in basic and translational science.

It can be appreciated that the scope of conditions of operation for the apparatus described herein may be programmed to enable multiple parameters to be applied to the organ either in combination or in sequence. Furthermore, the programming may be fixed in sequence, or it may be user-adjustable. Programming and data interface controls and displays can be displayed directly on the apparatus in the control section, via electronic interface to a computer or other instrument, via the internet, or by wireless connection.

From the foregoing, it will be observed that numerous variations and modifications may be effected without departing from the spirit and scope of the invention. It is to be understood that no limitation with respect to the specific apparatus illustrated herein is intended or should be inferred.

The invention claimed is:

1. A tissue or organ preservation system for circulating perfusate in contact with a tissue or organ, comprising: an organ chamber for containing an organ or tissue; a perfusate circuit comprising a perfusate pump; a perfusate reservoir at the base of the organ chamber for collecting perfusate exiting an organ or flowing past tissue, said perfusate reservoir in communication with the perfusion circuit; a support platform located within the organ chamber and located above the perfusate reservoir for supporting the organ or tissue; a heat exchanger locating a heat exchanger fluid in contact with at least one surface of the perfusate reservoir; an oxygenator mechanism disposed within the perfusate reservoir and configured to oxygenate the perfusate within the perfusate reservoir, the oxygenator mechanism comprises an elongated flexible gas conduit located below the support platform, a conduit wall of the conduit is an oxygen diffusion membrane through which oxygen is transferred to the perfusate adjacent the conduit within the perfusate reservoir, the conduit is arranged in an at least partially non-linear and overlapping configuration, the oxygenator mechanism is distinct from the perfusate pump; a perfusate stirring element disposed within the perfusate reservoir; and, a temperature equilibrating and oxygen enhancing perfusate stirring element disposed within the perfusate reservoir, and, a stirring drive motor configured to rotate the perfusate stirring member in one direction about an axis of rotation, wherein the elongated flexible gas conduit is gas permeable tubing, wherein the at least partially non-linear and overlapping configuration is a wound configuration, and wherein the spacing of the tubing is maintained by comb-like slots in the tubing supports.

2. A tissue or organ preservation system for circulating perfusate in contact with a tissue or organ, comprising: an organ chamber for containing an organ or tissue; a perfusate circuit comprising a perfusate pump; a perfusate reservoir at the base of the organ chamber for collecting perfusate exiting an organ or flowing past tissue, said perfusate reservoir in communication with the perfusion circuit; a support platform located within the organ chamber and located above the perfusate reservoir for supporting the organ or tissue; a heat exchanger locating a heat exchanger fluid in contact with at least one surface of the perfusate reservoir; an oxygenator mechanism disposed within the perfusate reservoir and configured to oxygenate the perfusate within the perfusate reservoir, the oxygenator mechanism comprises an elongated flexible gas conduit located below the support platform, a conduit wall of the conduit is an oxygen diffusion membrane through which oxygen is transferred to the perfusate adjacent the conduit within the perfusate reservoir, the conduit is arranged in an at least partially non-linear and overlapping configuration the oxygenator mechanism is distinct from the perfusate pump; a perfusate stirring element disposed within the perfusate reservoir; and, a temperature equilibrating and oxygen enhancing perfusate stirring element disposed within the perfusate reservoir, and, a stirring drive motor configured to rotate the perfusate stirring member in one direction about an axis of rotation, wherein support member comprises support legs extending into the perfusate reservoir; and wherein the elongated flexible gas conduit, gas permeable tubing for transporting oxygen from an oxygen supply source to the perfusate reservoir, the tubing is wound around the support legs within the perfusate reservoir; wherein the tubing spacing is maintained by comb-like slots in the support legs.

* * * * *